United States Patent [19]

Plapp, Jr.

[11] 4,152,454
[45] May 1, 1979

[54] INSECTICIDAL COMPOSITIONS COMPRISING N'-ARYL-N-METHYLFORMAMIDINES AND 3-PHENOXYBENZYL CARBOXYLATES

[75] Inventor: Frederick W. Plapp, Jr., College Station, Tex.

[73] Assignee: FMC Corporation, Philadelphia, Pa.

[21] Appl. No.: 898,595

[22] Filed: Apr. 21, 1978

Related U.S. Application Data

[63] Continuation of Ser. No. 753,037, Dec. 22, 1976, abandoned.

[51] Int. Cl.$^2$ .................. A01N 9/06; A01N 9/16; A01N 9/20; A01N 9/24
[52] U.S. Cl. ................................. 424/304; 424/311; 424/321; 424/326
[58] Field of Search .............. 424/326, 311, 304, 321

[56] References Cited

U.S. PATENT DOCUMENTS

| | | | |
|---|---|---|---|
| 3,358,011 | 12/1967 | Elliott | 424/311 |
| 3,378,437 | 4/1968 | Arndt et al. | 424/330 |
| 3,835,176 | 9/1974 | Matsuo et al. | 260/465 D |
| 3,937,813 | 2/1976 | Clark | 424/326 |
| 3,944,666 | 3/1976 | Montgomery et al. | 424/219 |
| 3,947,591 | 3/1976 | Rizzo et al. | 424/326 |
| 4,053,595 | 10/1977 | Zeck et al. | 424/216 |

FOREIGN PATENT DOCUMENTS 801946 1/1974 Belgium.
1150242 6/1963 Fed. Rep. of Germany.

OTHER PUBLICATIONS

Parham et al., Proceedings of the 8th Brit. Insect. and Fungic. Conf., Brit. Crop Protection Council, London, England, p. 659 (1975).
Knowles et al., J. Elon. Entomol. 66, 1245 (1973).

*Primary Examiner*—Albert T. Meyers
*Assistant Examiner*—D. W. Robinson
*Attorney, Agent, or Firm*—Richard L. Hansen; Henry R. Ertelt

[57] ABSTRACT

Compositions comprising, in combination, N'-aryl-N-methylformamidines and 3-phenoxybenzyl carboxylates exhibit synergistic insecticidal activity. The novel compositions are exemplified and their use for controlling insects is demonstrated.

6 Claims, No Drawings

INSECTICIDAL COMPOSITIONS COMPRISING N'-ARYL-N-METHYLFORMAMIDINES AND 3-PHENOXYBENZYL CARBOXYLATES

This is a continuation of application Ser. No. 753,037, filed Dec. 22, 1976, now abandoned.

BACKGROUND OF THE INVENTION

1. Field of the Invention

This invention pertains to the field of bioaffecting compositions; more specifically, it pertains to insecticidal compositions containing organic active ingredients comprising N'-aryl-N-methylformamidines and 3-phenoxybenzyl carboxylates and to the use of the compositions for controlling insects.

2. Description of the Prior Art

3-Phenoxybenzyl carboxylate insecticides, such as 3-phenoxybenzyl 3-(2,2-dihalovinyl)-2,2-dimethylcyclopropanecarboxylates, are of great interest currently because, unlike previous compounds of this type, such as the natural pyrethrins, they have good photo-oxidative stability. Pyrethrins have long been of interest because they are active against a wide range of insect species, they display relatively low toxicity toward mammals, and they do not leave harmful residues. However, pyrethrins and the newer 3-phenoxybenzyl carboxylates are very costly, and ways to increase their cost effectiveness are actively being sought.

Synergists are used commercially in combination with pyrethrins because they lessen the amount of insecticide required and thus reduce the cost at which insect control is achieved. Some of the most widely used synergists for pyrethrins are methylenedioxyphenyl compounds; piperonyl butoxide is a well-known example [U.S. Pat. No. 2,550,737]. More recently, mono(alkyl and alkenyl) mono-ω-alkynyl arylphosphonates were recognized as synergists [U.S. Pat. Nos. 3,885,031 and 3,944,666]. The latter also synergize the insecticidal activity of 3-phenoxybenzyl 3-(2,2-dichlorovinyl)-2,2-dimethylcyclopropanecarboxylate.

Control of insects of the order Lepidoptera, genus Heliothis, is important to the successful growth of cotton and other important crops. The tobacco budworm, *Heliothis virescens*, is a major late season pest of cotton. This insect is resistant to most insecticides now registered for use against it. The bollworm, *Heliothis zea*, is also a major cotton pest. Attempts to synergize insecticides against Heliothis have not been very successful. It is known, however, that the activity of pyrethrins and the synthetic pyrethroid, tetramethrin, against Heliothis can be increased by admixture of N'-(4-chloro-2-methylphenyl)-N,N-dimethylformamidine, chlordimeform [Plapp, *J. Econ. Entomol.*, 69, 91 (1976)], but neither pyrethrins nor tetramethrin are 3-phenoxybenzyl carboxylates.

*Bacillus thuringiensis* in combination with chlordimeform also exhibits synergism [Creighton, et al., *J. Econ. Entomol.*, 67, 102 (1974)]. Chlordimeform is an acaricide and an ovicide but has limited insecticidal activity. [Knowles, et al., *J. Econ. Entomol.*, 66, 1245 (1973); Wolfenbager, et al., ibid., 67, 445 (1973)].

SUMMARY OF THE INVENTION

It has now been discovered that novel compositions of matter comprising N'-aryl-N-methylformamidines and 3-phenoxybenzyl carboxylate insecticides are synergistic combinations, in that the compositions exhibit unexpectedly high insecticidal activity, as much as seven-fold higher than expected on the basis of simply additive activities. The compositions of matter within the scope of this invention comprise at least one N'-aryl-N-methylformamidine of the formula

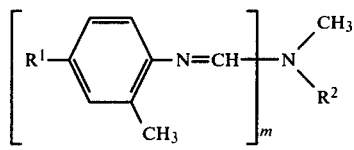

wherein
m is 1 or 2; and
when m is 1,
R¹ is chlorine or methyl, and R² is methyl, trichloromethylthio, or S-[N-((N-(4-chloro-2-methylphenyl)imino)methyl)-N-methylamino]thio, and
when m is 2,
R¹ is methyl and R² is absent;
combined with at least one 3-phenoxybenzyl carboxylate of the formula

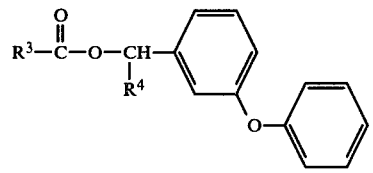

wherein R³ is a substituted isobutyl or cyclopropyl group, and R⁴ is hydrogen or cyano.

Examples of N'-aryl-N-methylformamidines which may be employed in this invention include N'-(4-chloro-2-methylphenyl)-N,N-dimethylformamidine, N'-(4-chloro-2-methylphenyl)-N-methyl-N-(trichloromethylthio)formamidine, N,N'-bis[(N-(4-chloro-2-methylphenyl)imino)methyl]-N,N'-dimethylsulfoxylic diamide, and N,N-bis[(N-(2,4-dimethylphenyl)imino)methyl]methylamine.

Examples of 3-phenoxybenzyl carboxylates which may be employed in this invention include 3-phenoxybenzyl 3-(2,2-dichlorovinyl)-2,2-dimethylcyclopropanecarboxylate, (−)-α-cyano-3-phenoxybenzyl (+)-cis-3-(2,2-dibromovinyl)-2,2-dimethylcyclopropanecarboxylate, α-cyano-3-phenoxybenzyl 2,2,3-trimethylcyclopropanecarboxylate, and α-cyano-3-phenoxybenzyl 2-(4-chlorophenyl)-3-methylbutanoate.

For the reason that the components are more readily available, compositions wherein the N'-aryl-N-methylformamidine is N'-(4-chloro-2-methylphenyl)-N,N-dimethylformamidine and the 3-phenoxybenzyl carboxylate is 3-phenoxybenzyl 3-(2,2-dichlorovinyl)-2,2-dimethylcyclopropanecarboxylate are especially advantageous.

As will be evident to those skilled in the art, formulated insecticides incorporating these compositions may also contain the solvents, dispersants, surfactants, and other adjuvants commonly employed in pesticides.

Although the insecticidal activity of the aforesaid 3-phenoxybenzyl carboxylates is enhanced by the admixture of a synergistic amount, as little as 10% by weight, of one of the aforesaid N'-aryl-N-methylformamidines, optimum synergism is obtained when the N'-aryl-N-methylformamidine: 3-phenoxybenzyl carboxylate ratio is between 1:2 and 20:1 by weight.

Also within the contemplation of this invention is the use of the aforesaid novel insecticidal compositions for controlling insects. For example, the insecticidal compositions of this invention may be used against insects of the order Lepidoptera, and within that order, use against insects of the genus Heliothis is especially effective.

In using the novel compositions to control insects, it is only necessary to achieve contact between the insects and an insecticidally effective amount of the composition.

The nature of these novel compositions and their use for controlling insects will become more evident by reference to the following nonlimiting Examples.

DESCRIPTION OF THE PREFERRED EMBODIMENTS

Insects employed in the following tests [See Plapp, J. Econ. Entomol., 64, 999 (1971).] were selected from stock colonies of the tobacco budworm and the bollworm. The test insects were third or fourth instar larvae weighing approximately 25–50 mg. The N'-aryl-N-methylformamidines and 3-phenoxybenzyl carboxylates were technical grade commercial materials. N'-(4-chloro-2-methylphenyl)-N,N-dimethylformamidine, hereinafter designated X, is described in U.S. Pat. No. 3,378,437. N'-(4-chloro-2-methylphenyl)-N-methyl-N-(trichloromethylthio)formamidine, hereinafter Y, and N,N-bis[(N-(2,4-dimethylphenyl)imino)methyl]methylamine are discussed in Parham, et al., Proceedings of the 8th British Insecticide and Fungicide Conference, British Crop Protection Council, 160 Great Portland Street, London W1N 6DT, England, 1975, p. 653. N,N'-Bis[(N-(4-chloro-2-methylphenyl)imino)methyl]-N,N'-dimethylsulfoxylic diamide, hereinafter Z, is described in U.S. Pat. No. 3,947,591. South African Pat. No. 73/3528 describes both 3-phenoxybenzyl 3-(2,2-dichlorovinyl)-2,2-dimethylcyclopropanecarboxylate and (−)-α-cyano-3-phenoxybenzyl (+)-cis-3-(2,2-dibromovinyl)-2,2-dimethylcyclopropanecarboxylate, designated A and B respectively hereinafter. α-Cyano-3-phenoxybenzyl 2,2,3-trimethylcyclopropanecarboxylate, hereinafter C, is disclosed in U.S. Pat. No. 3,835,176; while α-cyano-3-phenoxybenzyl 2-(4-chlorophenyl)-3-methylbutanoate, hereinafter D, is described in Belgian Pat. No. 801,946.

The N'-aryl-N-methylformamidines and 3-phenoxybenzyl carboxylates were dissolved separately or together in acetone. Varying quantities (0.2–0.3 ml) of the acetone solutions (3–5 different quantities of each solution) were pipetted into 20-ml glass vials of the type used for liquid scintillation counting. Small amounts of acetone were then added to the vials, and the vials were rolled until the acetone evaporated, depositing the solutes uniformly on the walls. Pieces of artificial Heliothis diet were then placed in each of four vials containing the same quantity of the same solute, together with one third or fourth instar larva, and the vials were plugged with cotton. The exposed insects were examined after 96 hours. The N'-aryl-N-methylformamidines alone were nontoxic at a dose of 100 μg/vial; thus $LD_{50}$'s were obtained by probit analyses based only on amounts of 3-phenoxybenzyl carboxylates in the vials. The results of tests against the tobacco budworm appear in Table 1, the results against the bollworm in Table 2. "Relative potency" is defined as $LD_{50}$ for the 3-phenoxybenzyl carboxylate used alone divided by $LD_{50}$ for the corresponding composition of this invention. Synergism is indicated by a relative potency greater than 1.

TABLE 1

Toxicity of 10:1 N'-Aryl-N-methylformamidine/3-Phenoxybenzyl Carboxylate Compositions Against the Tobacco Budworm

| | Composition | | | |
|---|---|---|---|---|
| | 3-Phenoxybenzyl Carboxylate | Formamidine | $LD_{50}$ μg/vial | Relative Potency |
| Test 1 | A | none | 5.7 | — |
| | A | X | 0.81 | 7.0 |
| Test 2 | A | none | 3.8 | — |
| | A | Y | 0.72 | 5.2 |
| | A | Z | 1.2 | 3.2 |
| Test 3 | B | none | 0.24 | — |
| | B | X | 0.05 | 4.8 |
| Test 4 | C | none | 3.9 | — |
| | C | X | 1.7 | 2.3 |
| Test 5 | D | none | 2.7 | — |
| | D | X | 0.92 | 2.9 |

TABLE 2

Toxicity of 10:1 N'-Aryl-N-methylformamidine/3-Phenoxybenzyl Carboxylate Compositions Against the Bollworm

| | Composition | | | |
|---|---|---|---|---|
| | 3-Phenoxybenzyl Carboxylate | Formamidine | $LD_{50}$ μg/vial | Relative Potency |
| Test 6 | A | none | 5.1 | — |
| | A | X | 2.1 | 2.4 |

I claim:

1. Synergistic insecticidal composition consisting essentially of between about 1 and 10 parts N'-aryl-N-methylformamidine selected from the group consisting of N'-(4-chloro-2-methylphenyl)-N,N-dimethylformamidine, N'-(4-chloro-2-methylphenyl)-N-methyl-N-(trichloromethylthio)formamidine, N,N'-bis[(N-(4-chloro-2-methylphenyl)-imino)methyl]-N,N'-dimethylsulfoxylic diamide, and N,N-bis[(N-(2,4-dimethylphenyl)imino)methyl]-methylamine, and 1 part 3-phenoxybenzyl 3-(2,2-dichlorovinyl)-2,2-dimethylcyclopropanecarboxylate.

2. Synergistic insecticidal composition consisting essentially of between about 1 and 10 parts N'-(4-chloro-2-methylphenyl)-N,N-dimethylformamidine, and 1 part (−)-α-cyano-3-phenoxybenzyl (+)-cis-3-(2,2-dibromovinyl)-2,2-dimethylcyclopropanecarboxylate.

3. Synergistic insecticidal composition consisting essentially of about 10 parts N'-(4-chloro-2-methylphenyl)-N,N-dimethylformamidine and 1 part α-cyano-3-phenoxybenzyl 2,2,3-trimethylcyclopropanecarboxylate.

4. Synergistic insecticidal composition consisting essentially of about 10 parts N,N'-bis[N-(4-chloro-2-methylphenyl)imino)methyl]-N,N'-dimethylsulfoxylic diamide and 1 part (−)-α-cyano-3-phenoxybenzyl (+)-cis-3-(2,2-dibromovinyl)-2,2-dimethylcyclopropanecarboxylate.

5. A method for controlling larvae of the genus Heliothis which comprises contacting the larvae with an insecticidally effective amount of a composition of claim 1.

6. A method for controlling larvae of the genus Heliothis which comprises contacting the larvae with an insecticidally effective amount of a composition of claim 2, 3 or 4.

* * * * *